US005453281A

United States Patent [19]

Whistler

[11] Patent Number: 5,453,281
[45] Date of Patent: Sep. 26, 1995

[54] COMPOSITIONS UTILIZING SMALL GRANULE STARCH

[75] Inventor: Roy L. Whistler, West Lafayette, Ind.

[73] Assignee: Lafayette Applied Chemistry, Inc., West Lafayette, Ind.

[21] Appl. No.: 852,691

[22] Filed: Mar. 17, 1992

[51] Int. Cl.$^6$ .............. A61K 9/14; A61K 9/16; A61K 9/20; A61K 7/02

[52] U.S. Cl. .............. 424/465; 424/499; 424/69; 514/951

[58] Field of Search .............. 424/465, 469, 424/470, 499, 458; 428/402; 426/661

[56] References Cited

U.S. PATENT DOCUMENTS

| | | | |
|---|---|---|---|
| 4,072,535 | 2/1978 | Short et al. | 106/210 |
| 4,122,157 | 10/1978 | Huber | 424/472 |
| 4,369,308 | 1/1983 | Trubiano | 536/106 |
| 4,383,111 | 5/1983 | Takeo et al. | 536/102 |
| 4,551,177 | 11/1985 | Trubiano et al. | 106/210 |
| 4,755,397 | 7/1988 | Eden et al. | 424/488 |
| 4,913,896 | 4/1990 | Harvey | 424/69 |
| 4,985,082 | 1/1991 | Whistler | 127/33 |

FOREIGN PATENT DOCUMENTS 0182296  11/1985  European Pat. Off. .

OTHER PUBLICATIONS

Jane, J. et al, Preparation and Properties of Small–Particle Corn Starch, Cereal Chemistry, 1992: 69 (3) 280–283.

"Quinoa (*Chenopodium quinoa*) Starch–Physico–Chemico Properties And Functional Characteristics", starch/Stärke 42, Nr. 3, pp. 81–86, K. Lorenz.

"New Starches, V. Properties of the Small Granules from *Amaranthus retroflexus*", Cereal Chemistry, vol. 47, No. 5, 1970, P. V. Subba Rao and K. J. Goering.

"Characterization of Starch Granules from Waxy, Nonwaxy, and Hybrid Seeds of *Amaranthus hypochondriacus* L.", *Agric. Biol. Chem.*, 49(7), 1965, Yotaro Konishi et al.

"Experiences on Isolation, Properties and Cross–linkage of Fine Granule Starches", Institute for Starch and Potato Technology, by E. Wilhelm (abstract).

"A Comparative Evaluation of Some Starches as Disintegrants for Double Compressed Tablets", *Chem. Abstracts*, 110:179445p, vol. 110, 1989, M. A. F. Gadalla, et al. (abstract).

"Study of the Tableting Properties of Cassava Starch V. Stability of Various Drugs in Modified Cassace Starch Used As a Direct Compression Excipient", *Chem. Abstracts*, 115:214682r, vol. 115, 1991, S. A. Megwa, et al. (abstract).

"Starch and Grain Powders as Carriers of Oils Useful in Foods, Cosmetics and Pharmaceuticals", *Chem. Abstracts*, 106:137250h, vol. 106, 1987, Yamashita, et al., (abstract).

"Manufacture of Body Powders Containing Fine Starch Particles", *Chem. Abstracts*, 111:45059c, vol. 111, 1989, S. Kishida, et al., (abstract).

*Primary Examiner*—Edward J. Webman
*Attorney, Agent, or Firm*—Barnes & Thornburg

[57] ABSTRACT

Small granule starch having a mean granule size of less than about 5 microns is substituted for binder excipients in tabletting compositions or the talc or granular starch ingredients of art recognized cosmetic/dusting powder compositions to provide improved compositions. Small granular starch is used as a binder with an orally active ingredient and other optional excipients to provide a tabletting mixture which can be compressed into tablets having excellent hardness and favorable disintegration characteristics. The use of small granule starches as a substitute for art-recognized starch and/or talc carriers in cosmetic/body powders provide compositions with enhanced coverage and a softer feel when applied to the skin.

7 Claims, No Drawings

COMPOSITIONS UTILIZING SMALL GRANULE STARCH

FIELD OF THE INVENTION

This invention relates to improved starch powder-based compositions. More particularly, this invention is directed to the use of small granule starch as a multifunctional excipient for improved tabletting and cosmetic/dusting powder compositions. Compressed tablets utilizing small granule starch as a binder exhibit high hardness and good disintegration properties. Cosmetic powders utilizing small granular starch as a substitute for talc or other common granular starch ingredients exhibit an improved silky feel when applied to the skin.

BACKGROUND OF THE INVENTION

Tablets usually consist of several inert materials, referred to as excipients, in addition to an orally active ingredient present in amounts sufficient to accomplish the desired therapeutic or nutritive effect. Tabletting excipients are generally classified according to their function, such as diluents (also called bulking agents and fillers), binders which hold the ingredients together in the compressed tablet, disintegrants which help facilitate the break-up of the tablet when placed in a fluid environment to release the active ingredient, and lubricants to improve the release of the compressed tablet from the die and punches. In addition, tablets may contain other substances intended to improve the tabletting process. For example, flow additives, flavors, sweeteners and anti-oxidants can be added.

Tabletting and some capsule filling operations are based on the ability of certain powders to bind under compression. Compressed tablets may be prepared by wet granulation, dry granulation, or direct compression. The wet granulation process typically includes mixing the components, usually in powder form, preparing the granulating binder solution, thoroughly mixing the components with the granulating binder solution to form a dough, coarse screening the mass through a sieve, drying, grinding, adding the lubricant and compressing the tablets from the resulting mixture. Dry granulation involves the steps of mixing the powder components, compressing the mixture into hard slugs, grinding the slugs into desired particle size, screening, adding other excipients if necessary, and compressing the mixture into tablets. The most preferred and economical tabletting method, direct compression, requires only two steps—mixing the dry components and compressing the mixture into tablets.

Typical direct compression binders include microcrystalline cellulose, compressible sugars, certain calcium salts, lactose and dextrose. Of these, microcrystalline cellulose has found wide commercial use. That excipient also displays good disintegration properties. However, tablets made with microcrystalline cellulose tend to have a dull rough surface. Other good binders include calcium phosphates and compressible sugars. One disadvantage of the calcium salt binders is that they do not allow the preparation of tablets with high levels of active ingredients and generally require the use of disintegrants. The sugars present a darkening problem and tend to increase in hardness with age. Mannitol and sorbitol have certain taste advantages, but they lack binding properties and require a disintegrant. They suffer too from the disadvantages of being expensive and hydroscopic.

Starch as a binder should not be confused with starch as a disintegrant or diluent since different properties are required for each use; however some modified starch binders can also function as disintegrants. The most important property required in a binder is compressibility. Generally speaking, granular starches and conventional pre-gelatinized (i.e., cooked, non-granular, cold-water-dispersible starches) do not bind well under direct compression. Cooked non-granular starches which are satisfactory as binders, are not satisfactory as disintegrants. They tend to hydrate rapidly and in many cases form a tacky film on the tablet surface, thus preventing water penetration into the tablet to aid in disintegration.

Various attempts have been made to modify starches to improve their binding/disintegration properties. These have included chemical and physical modification of the starch. Physically modified starch, partially cold-water-swelling, cold-water-soluble compacted starches are reportedly useful as binder-disintegrants for direct compression tabletting (see U.S. Pat. Nos. 3,622,677 and 4,072,535). Physically modified starches, which are cold-water-swellable, but limited in their coldwater solubility, are useful as disintegrants for various tabletting methods (see U.S. Pat. No. 4,383,111), but not as binders. Chemically modified starches such as starch ester or ether derivatives and cross-linked pregelatinized starches, are useful as disintegrants but not as binders. Starch fractions, such as non-granular amylose, are also reportedly useful as binder-disintegrants in direct compression or double compression (dry slugging) tabletting processes (see U.S. Pat. No. 3,490,742), but are not suitable as wet granulation binders.

There is, therefore, a need for a multifunctional compressible starch which is suitable for use as a binder in tabletting compositions, especially those prepared for direct compression tabletting methods.

It is one object of this invention to provide an improved tabletting composition utilizing a binder comprising small granule starch. It is another object of this invention to provide a compressed tablet utilizing a granular starch having a mean granule size of less than about 5 microns as the binder excipient. It is still another object of this invention to provide improved compressed tablets utilizing a small granule starch binder which imparts not only excellent tablet hardness, but further provides good disintegration characteristics.

Starch has also been used in many different forms for centuries as a cosmetic/body powder ingredient. In the 17th and 18th centuries wheat starch and later potato and rice starch were used for such compositions. Starch dyed in various colors was used in early England for cosmetic purposes. Starches used as body powders and more particularly as face powders gave a generally silky smooth feeling to the skin. Today the most important ingredient in most body powders in the field of human skin care is talc, a natural hydrous magnesium silicate. The excellent slip characteristics of cosmetic grade talc provides a lubricant action and a smooth feel to the touch. However, because pure talc powder does not absorb moisture well, many have employed powders consisting principally of starch and fragrance or other cosmetically functional ingredients with other added excipients to promote flowability and resistance to bacteria attack. The problem with the use of starch in cosmetic/body powders is that starches do not slip or disperse as readily as talc, thereby not giving the smooth-to-the-touch characteristic that is an important characteristic of cosmetic/body powder compositions.

The use of small granular starch, particularly amaranth or quinoa starch in cosmetic/body powder composition has been found to provide compositions having enhanced cosmetic functionality and sensory (smoothness) characteristics. Thus it is another object of this invention to improve cosmetic/body powder compositions utilizing small granule starch as a substitute for at least a portion of the talc or granular starch ingredients utilized in the cosmetic/body powder formulations now known in the art. It is still another object of this invention to provide improved cosmetic/body powder compositions comprising small granule starch in combination with at least one cosmetically functional ingredient.

SUMMARY OF THE INVENTION

The present invention provides for the use of small granule starch (granular starch having a mean granule size less than about 5 microns) as a multifunctional excipient for improved tabletting and cosmetic/dusting powder compositions. In one embodiment of the invention small granule starch is used as a binder for compressed tablets. The use of small granule starches, for example, amaranth starch, quinoa starch or the small granule fraction of wheat starch as a binder in tabletting compositions, finds particular applications in compositions prepared for direct compression tabletting. Small granule starches also find application in accordance with this invention as wet granulation and dry granulation binders. The small granule starch is admixed with an orally active ingredient and other optional art-recognized excipients to provide a mixture which can be compressed into tablets having excellent hardness characteristics [at least 5 kilopond (kp)/cm$^2$]) and as well favorable disintegration characteristics.

When small granule starches are used as a cosmetic/body powder ingredient as a substitute in whole or in part for talc or the granular starch components of known cosmetic/dusting powder formulations the resultant powders when applied to the skin exhibit enhanced coverage characteristics and a more smooth/silky feel.

DETAILED DESCRIPTION OF THE INVENTION

The present invention is based on the discovery that certain granular starches having a mean granular size of less that about 5 micron can be used as multi-functional excipients in tabletting and cosmetic/dusting powder compositions. Suitable small granule starches for use in accordance with the present invention include particularly granular starch from amaranth having a granular size of about 1 to about 3 microns in diameter, granular starch from quinoa having a granule size of about 1 to about 2.5 microns in diameter, and the small granule fraction of wheat starch having a granule size of about 2 to about 5 microns in diameter. The starches can be isolated from the respective seeds by wet milling in much the same way as starch is produced commercially from corn or potato. Basically the starch bearing seeds are steeped and disintegrated by grinding or by high speed shearing. The starch is separated from the aqueous phase following removal of fiber by screening. As is known in the art, the small granule fraction of wheat starch can be obtained by size classification in a hydrocyclone using an air or water slurry or other size classification processes well known in the art.

The small granule starches can be used in preparation of the improved tabletting and cosmetic/dusting powder compositions with or without additional modification. It is critical for functional use in accordance with this invention only that the small granular starch maintain its non-gelatinized granular character. Thus, for example the granular starch can be chemical modified by crosslinking with art recognized starch crosslinking agents or otherwise derivitized with one or more of the art recognized starch ether-forming or ester-forming reagents. In applications where color of the small granule starch component is important, the small granular starch can be subjected to bleaching conditions with, for example, hypochlorite or other mild bleaching agents.

The small granule starches utilized in accordance with the present invention to prepare improved tabletting compositions and cosmetic/dusting powders is selected to have a mean granule size less than 5 microns, more preferably between about 1 and about 3 microns. Granular starch harvested by wet milling of amaranth and quinoa seeds are most preferred.

As mentioned above, tabletting compositions comprising an orally active ingredient, a binder and, optionally, other excipients for use in a dry granulation, wet granulation or direct compression tabletting process are well known in the art. It is generally recognized in the art that granular starches in their natural state (i.e., without pretreatment by physical or chemical modification) are not acceptable binders for tabletting compositions. The present invention is based on the discovery that certain small granule starches having a mean granule size of about 5 microns do perform well as a binder excipient for tabletting compositions and as a carrier for cosmetically functional ingredients in cosmetic/dusting powders. Tablets formed from tabletting compositions comprising a small granule starch binder have been shown as well to have good disintegration characteristics.

The term "orally active ingredient" as used in describing the present invention refers to any chemical compound or composition having a nutritive or therapeutic effect on oral administration. The term "orally active ingredient" thus is intended to encompass analgesics, decongestants, antihistamines, antitussives, antacids, gastric protectants, bronchial dialators, sleep-aids, vitamins, laxatives, antibiotics, antispasmolytics, and the like. Typically such compositions include the orally active ingredient and the small granule starch binder alone or in combination with microcrystalline cellulose, and a suitable lubricant. The amount of small granule starch to be utilized as a binder in accordance with the present invention parallels the levels of binder on a weight-for-weight basis in art recognized tabletting compositions. The small granular starch can be substituted for at least a portion, preferably a major portion of the binder excipient to provide a tabletting composition that can be compressed, for example on a Carver press or on a rotary tabletting machine in accordance with art recognized practices to provide the improved tablets in accordance with this invention. Most preferably the small granule starch binder is either used as the sole binder excipient in the tabletting compositions or in combination with microcrystalline cellulose.

The tablets prepared in accordance with this invention utilizing a small granule starch binder typically exhibit a tablet hardness of greater than 5 kilopond (kp)/cm$^2$, more preferably a tablet hardness of greater than 10, most preferably about 10 to about 20 kp/cm$^2$ and a disintegration time of less than 30 minutes, more preferably less than 15 minutes as measured utilizing the standard USP disintegration test in water.

Further in accordance with this invention it has been discovered that small granule starches can be substituted for at least a portion of a granular starch or talc carrier ingredient in a cosmetic or dusting powder composition containing an effective amount of a cosmetically functional substance such as a fragrance or a coloring agent. The use of small granule starches having a granule size of less than about 5 microns as a carrier for cosmetically functional substances in cosmetic/dusting powders provide a powder formulation that exhibits an unusually satiny or silky feel when applied to the skin and as well more efficient coverage of the area of the skin to which the cosmetic formulation is applied. Preferred small granular starches for use in the improved cosmetic/dusting powder compositions in accordance with this invention are the granular starches derived from amaranth and quinoa seed, optionally chemically derivitized to enhance resistance to degradation or to enhance compatibility with other composition ingredients.

The improved cosmetic or dusting powder composition in accordance with this invention can be prepared simply by substituting small granular starch for at least a portion of the granular starch or talc ingredient of art recognized cosmetic or dusting powder compositions. Preferably the small granular starch is substituted for at least a 50% preferably more than 75% of the talc or starch carrier utilized in the prior art composition.

EXAMPLE 1

A preliminary evaluation of the binder functionality of amaranth starch compared to corn starch was conducted by forming 500 milligram tablets using a Carver press. The tablets were formed utilizing amaranth starch alone or in combination with 10% by weight of carboxymethyl cellulose (Avicel), and corn starch alone or in combination with 10% by weight of Avicel. The amaranth starch formulations were compressed at 1,000 pound pressure while the corn starch formulations were compressed at 3,000 pound pressure in the tablet-forming process. The tablets formed with amaranth starch exhibited an average hardness of 8.06 $kp/cm^2$ while the amaranth/Avicel blend exhibited a hardness value of 7.76 $kp/cm^2$. The corn starch composition, on the other hand, exhibited a hardness value of 1.62 $kp/cm^2$; the corn starch/Avicel blend exhibited an average hardness of 2.8 $kp/cm^2$. Disintegration time for the amaranth and amaranth/Avicel blends were 17 minutes, 9 seconds and 14 minutes, 6 seconds, respectively. Disintegration times for the corn starch and corn starch/Avicel blends were each measured at 37 seconds.

EXAMPLE 2

This example describes the comparison of hardness and disintegration characteristics of tablets formed utilizing amaranth starch alone or in combination with carboxymethyl cellulose. In each instance the tabletting composition was first dry blended and compressed singly on a Carver press into 500 milligram tablets at varying compression pressures. Three tabletting compositions were prepared:

A. Amaranth starch alone;

B. Amaranth starch plus 5% by weight microcrystalline cellulose (Avicel 101); and C. Amaranth starch plus 10% by weight phenylpropanolamine hydrochloride.

The hardness test data and disintegration time data for those compositions is summarized below in Table 1.

| Composition/Tabletting Pressure (lbs) | Hardness ($kp/cm^2$) | Disintegration Time (USP) |
|---|---|---|
| A/200 | 17.9 | 14 minutes, 12 seconds |
| B/200 | 15.9 | 15 minutes, 7 seconds |
| B/1500 | 9.52 | 14 minutes, 46 seconds |
| C/1500 | 10.3 | 20 minutes, 1 second |

Dissolution tests were carried out utilizing the USP Dissolution Method II for 30 minutes at 100 rpm in water. One hundred percent of the phenylpropanolamine hydrochloride was released in 30 minutes.

EXAMPLE 3

This example shows the use of small granule starch binder to prepare compressed tablets containing active ingredients.

Vitamin C Tablets

Direct compression tablets are prepared by dry blending 50 parts ascorbic acid, 49 parts amaranth starch and 1 part stearic acid and tabletted.

Wet granulation tablets are prepared by dry blending 90 parts ascorbic acid and 10 parts amaranth starch, granulating with 12–13% water in a Hobart mixer using speed #1, precompacting the granulate by passing it through the grinder attachment of the Hobart, oven drying at 100° C. to less than 0.6% moisture, and grinding through a #20 sieve on a #100 sieve. A total of 98.8 parts of the above ground dry granulate is dry blended with 1 part stearic acid and 0.2 part magnesium stearate and tabletted.

Acetaminophen Tablets

Dry compression tablets are prepared by dry blending 59 parts acetaminophen, 0.55 part Cabosil EH-5 (amorphous fumed silica) and 0.55 part silica gel and screening through a #20 sieve. A mixture of 38.3 parts amaranth starch, 1.05 part stearic acid and 0.55 part magnesium stearate is added to the mixture, screened through the #20 sieve and tabletted.

The preferred embodiments of the invention have been described above in detail. Various modifications and improvements thereto will become readily apparent to those skilled in the art. The foregoing examples are intended to be non-limiting and exemplary of the invention described in the foregoing specification and claimed below.

I claim:

1. In a compressed tablet formed by a tabletting process including dry granulation, wet granulation, or direct compression of a tabletting composition comprising an orally active ingredient and a binder ingredient, the improvement wherein the binder ingredient is selected from the group consisting of non-gelatinized quinoa starch granules, amaranth starch granules and the small granule fraction of wheat starch, said granular starch binder ingredient having a mean granule size of less than 5 microns.

2. The improvement of claim 1 where the binder is quinoa or amaranth starch granules.

3. A compressed tablet comprising an orally active ingredient and a binder comprising non-gelatinized starch granules having a mean granule size less than 5 microns and selected from the group consisting of quinoa starch granules, amaranth starch granules, and the small granule fraction of wheat starch, said binder being present in an amount effective to provide a tablet hardness of greater than 5 kp/cm$^2$ and a disintegration time of less than 30 minutes.

4. The tablet of claim 3 wherein the binder is quinoa or amaranth starch granules.

5. The tablet of claim 4 having a disintegration time of less than 15 minutes.

6. The tablet of claim 3 having a hardness of about 10 to about 20 kp/cm$^2$.

7. The tablet of claim 6 wherein the binder is amaranth starch.

* * * * *